United States Patent
Hong et al.

(10) Patent No.: US 10,953,069 B2
(45) Date of Patent: Mar. 23, 2021

(54) METHOD FOR TREATING LUNG CANCER

(71) Applicant: NATIONAL CHENG KUNG UNIVERSITY, Tainan (TW)

(72) Inventors: Jiann-Ruey Hong, Tainan (TW); Hsuan-Wen Chiu, Tainan (TW); Yu-Chin Su, Tainan (TW)

(73) Assignee: NATIONAL CHENG KUNG UNIVERSITY, Tainan (TW)

( * ) Notice: Subject to any disclaimer, the term of this patent is extended or adjusted under 35 U.S.C. 154(b) by 0 days.

(21) Appl. No.: 16/590,928

(22) Filed: Oct. 2, 2019

(65) Prior Publication Data

US 2020/0108116 A1 Apr. 9, 2020

Related U.S. Application Data

(60) Provisional application No. 62/741,782, filed on Oct. 5, 2018.

(51) Int. Cl.
*A61K 38/08* (2019.01)
*A61K 38/16* (2006.01)
*A61P 35/00* (2006.01)
*A61K 9/00* (2006.01)
*A61K 45/06* (2006.01)

(52) U.S. Cl.
CPC ............ *A61K 38/08* (2013.01); *A61K 9/0019* (2013.01); *A61K 38/162* (2013.01); *A61P 35/00* (2018.01); *A61K 45/06* (2013.01)

(58) Field of Classification Search
CPC ...... A61K 38/08; A61K 38/162; A61K 45/06; A61K 9/0019; A61P 35/00
See application file for complete search history.

(56) References Cited

U.S. PATENT DOCUMENTS

2007/0003550 A1* 1/2007 Antonia ............... A61P 43/00
424/145.1

OTHER PUBLICATIONS

Lee et al. Arginine-conjugated albumin microspheres inhibits proliferation and migration in lung cancer cells. Am J Cancer Res. 2013. vol. 3, No. 3, pp. 266-277. (Year: 2013).*
Koparal et al. Effects of carvacrol on a human non-small cell lung cancer (NSCLC) cell line, A549, Cytotechnology vol. 43, pp. 149-154. (Year: 2003).*
Condon et al. Lung dendritic cells at the innate-adaptive immune interface. JLB Journal of Leuckocyte Biology, 2011, vol. 90, No. 5, pp. 883-895. (Year: 2011).*
Zarogoulidis et al. Treatment of non-small cell lung cancer (NSCLC), J Thorac Dis, vol. 5, No. S4, pp. S389-S396. (Year: 2013).*
Hsuan-Wen Chiu, Yu-Chin Su, and Jiann-Ruey Hong, "Betanodavirus B2 protein triggers apoptosis and necroptosis in lung cancer cells that suppresses autophagy", Research Paper, pp. 94129-94141 year: 2017.
Office Action dated Nov. 13, 2019 for the corresponding Taiwan Patent Application No. 107135310.
Search report dated Nov. 13, 2019 for the corresponding Taiwan Patent Application No. 107135310.
English translation of the search report dated Nov. 13, 2019 for the corresponding Taiwan Patent Application No. 107135310.
Oncotarget 2017;8(55):94129-94141.
Apoptosis 2014;19:1457-1470.

* cited by examiner

*Primary Examiner* — Marcela M Cordero Garcia
(74) *Attorney, Agent, or Firm* — WPAT, P.C., Intellectual Property Attorneys; Anthony King

(57) ABSTRACT

The present disclosure provides a method for treating lung cancer in a subject in need of such treatment includes administering to the subject a pharmaceutical composition. The pharmaceutical composition includes an effective amount of a betanodavirus B2 protein or a fragment thereof, or a nucleic acid molecule encoding the betanodavirus B2 protein or the fragment and optionally a pharmaceutically acceptable carrier or excipient.

7 Claims, 4 Drawing Sheets

**Specification includ

SEQUENCE LISTING

```
<160> NUMBER OF SEQ ID NOS: 7

<210> SEQ ID NO 1
<211> LENGTH: 10
<212> TYPE: PRT
<213> ORGANISM: betanodavirus

<400> SEQUENCE: 1

Arg Thr Phe Val Ile Ser Ala His Ala Ala
1               5                   10
```

```
<210> SEQ ID NO 2
<211> LENGTH: 228
<212> TYPE: DNA
<213> ORGANISM: betanodavirus
<220> FEATURE:
<221> NAME/KEY: CDS
<222> LOCATION: (1)..(225)

<400> SEQUENCE: 2 atg gaa caa atc caa caa gcg atc gat cag cac ctc gtc gag ctc gag     48
Met Glu Gln Ile Gln Gln Ala Ile Asp Gln His Leu Val Glu Leu Glu
1               5                   10                  15 cag ctc ttc cag gtg atg atg gac acg cgc gtc gct ctc ggc gga gtg     96
Gln Leu Phe Gln Val Met Met Asp Thr Arg Val Ala Leu Gly Gly Val
            20                  25                  30 acc gcg atc cag gta aac gag atg cgc ac

-continued

```
Leu Val

<210> SEQ ID NO 6
<211> LENGTH: 25
<212> TYPE: PRT
<213> ORGANISM: betanodavirus

<400> SEQUENCE: 6

Val Asn Glu Met Arg Thr Phe Val Ile Ser Ala His Ala Ala Ala Arg
1               5                   10                  15

Arg Leu His Val Leu Ser Arg Arg Phe
            20                  25

<210> SEQ ID NO 7
<211> LENGTH: 15
<212> TYPE: PRT
<213> ORGANISM: betanodavirus

<400> SEQUENCE: 7

Val Asn Glu Met Ala Arg Arg Leu His Val Leu Ser Arg Arg Phe
1               5                   10                  15
```

METHOD FOR TREATING LUNG CANCER

BACKGROUND

1. Field of the Disclosure

The present disclosure relates to a cancer treatment, and more particularly to a method for treating lung cancer.

2. Description of the Related Art

In many countries, the prevalence rate of lung cancer is fairly large and further increasing year by year. Among the kinds of lung cancer, non-small cell lung cancer (NSCLC) is one of the main causes of cancer death, and its incidence is increasing. Surgery, radiotherapy, and chemotherapy are the major treatment methods to reduce lung cancer mortality.

Accordingly, there is a strong need for the development of therapeutic drugs practicably effective for the treatment of lung cancers.

SUMMARY

In some embodiments of the present disclosure, a method for treating lung cancer in a subject in need of such treatment includes administering to the subject a pharmaceutical composition. The pharmaceutical composition includes an effective amount of a betanodavirus B2 protein or a fragment thereof, or a nucleic acid molecule encoding the betanodavirus B2 protein or the fragment and optionally a pharmaceutically acceptable carrier or excipient.

In some embodiments of the present disclosure, a pharmaceutical composition for treating lung cancer is provided. The pharmaceutical composition includes an effective amount of a betanodavirus B2 protein or a fragment thereof, or a nucleic acid molecule encoding the betanodavirus B2 protein or the fragment and optionally a pharmaceutically acceptable carrier or excipient.

The present disclosure also provides use of a betanodavirus B2 protein or a fragment thereof, or a nucleic acid molecule encoding the betanodavirus B2 protein or the fragment in the manufacture of a medicament of the treatment of lung cancer.

BRIEF DESCRIPTION OF THE DRAWINGS

Aspects of some embodiments of the present disclosure are best understood from the following detailed description when read with the accompanying figures. It is noted that various structures may not be drawn to scale, and dimensions of the various structures may be arbitrarily increased or reduced for clarity of discussion.

DETAILED DESCRIPTION

Figure 1:
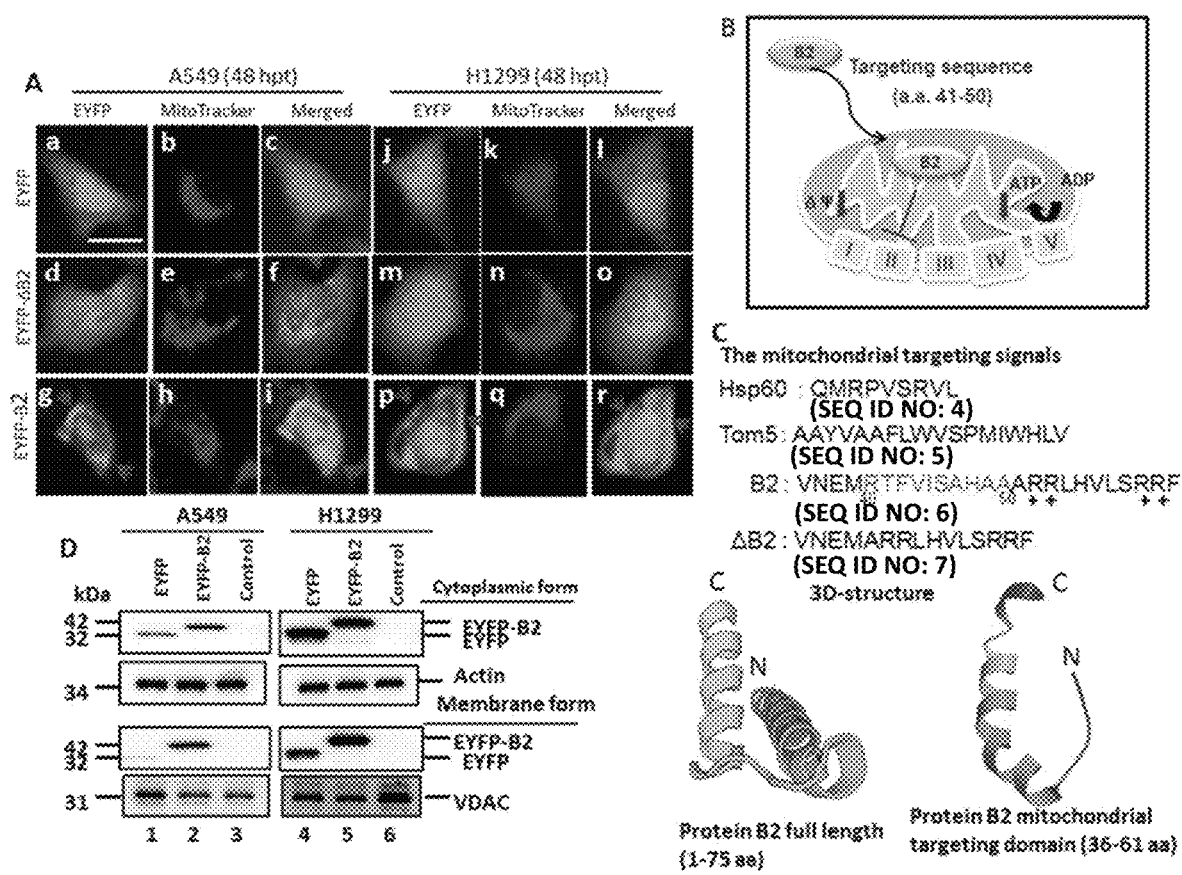
FIG. 1: MitoTracker staining indicates the RGNNV B2 protein targets the mitochondria in human lung cancer cells. Analysis of mitochondrial targeting of the EYFP-B2 fusion protein at 48 h post-transfection indicated yellow fluorescence in about 4-5% of A549 cells (A: g-i and d; indicated by arrows) and H1299 cells (A: p-r) relative to cells with EYFP (A: a-c, in A549 cells; A: j-l, in H1299 cells) and EYFP-ΔB2 (de141RTFVISAHAA50) (A: d-f, in A549 cells; A: m-o, in H1299 cells). Phase-contrast images of EYFP-B2 transfected cells at 36 h post-transfection shows that the EYFP-B2 fusion protein targets mitochondria (indicated by arrows; A: i in A549 cells; A: r in H1299 cells). Scale bar: 10 μm. (B) RGNNV B2 protein construct used for mitochondrial targeting. (C) Various constructs of wild type and mutant forms of the RGNNV B2 protein used to identify the mitochondrial targeting sequence. The 3D-structure of full length of RGNNV protein B2 (1-75 aa) and B2 mitochondria targeting domain (36-61 aa) alone (see Materials and Methods) were shown, and that alpha helix also existing. N: N terminus; C: C terminus. (D) Immunoblotting using monoclonal antibodies against EYFP shows the protein distribution in mitochondrial and cytosolic fractions at 48 h post-transfection. The internal controls were actin (cytosolic fraction) and VDAC (mitochondrial membrane fraction). EYFP alone (negative control; lanes 1 and 4); EYFP-B2 (lanes 2 and 5), controls without vector (A549 and H1299 cells; lanes 3 and 6).

The present disclosure provides a method for treating lung cancer in a subject in need of such treatment includes administering to the subject a pharmaceutical composition. The pharmaceutical composition includes an effective amount of a betanodavirus B2 protein or a fragment thereof, or a nucleic acid molecule encoding the betanodavirus B2 protein or the fragment and optionally a pharmaceutically acceptable carrier or excipient.

The present disclosure provides a pharmaceutical composition for treating lung cancer. The pharmaceutical composition includes an effective amount of a betanodavirus B2 protein or a fragment thereof, or a nucleic acid molecule encoding the betanodavirus B2 protein or the fragment and optionally a pharmaceutically acceptable carrier or excipient.

The present disclosure also provides use of a betanodavirus B2 protein or a fragment thereof, or a nucleic acid molecule encoding the betanodavirus B2 protein or the fragment in the manufacture of a medicament of the treatment of lung cancer.

"Optional" or "optionally" means that the subsequently described event or circumstance may or may not occur, and that the description includes instances where said event or circumstance occurs and instances where it does not. For example, the phrase "optionally comprising an agent" means that the agent may or may not exist. The term "subject" as used herein denotes any animal, preferably a mammal, and more preferably a human. The examples of subjects include humans, non-human primates, rodents, guinea pigs, rabbits, sheep, pigs, goats, cows, horses, dogs and cats.

The term "treating" or "treatment" as used herein denotes reversing, alleviating, inhibiting the progress of, or improving the disorder, disease or condition to which such term applies, or one or more symptoms of such disorder, disease or condition.

In some embodiments, the term "lung cancer" refers to all kinds of lung cancer or lung carcinoma, including non-small cell lung cancers (e.g. squamous cell carcinoma, adeno carcinoma, large cell carcinoma, etc.) and small cell lung cancer. Preferably, the lung cancer is non-small cell lung cancer.

The pharmaceutical composition of the invention can be formulated with suitable carriers, excipients, and other agents that provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles, DNA conjugates, anhydrous absorption pastes, oil-in-water and water-in-oil emulsions, emulsions carbowax (polyethylene glycols of various molecular weights), semi-solid gels, and semi-solid mixtures containing carbowax.

The term "effective amount" of an active ingredient as provided herein means a sufficient amount of the ingredient to provide the desired regulation of a desired function. As will be pointed out below, the exact amount required will vary from subject to subject, depending on the disease state, physical conditions, age, sex, species and weight of the subject, the specific identity and formulation of the composition, etc. Dosage regimens may be adjusted to induce the optimum therapeutic response. For example, several divided doses may be administered daily or the dose may be proportionally reduced as indicated by the exigencies of the therapeutic situation. Thus, it is not possible to specify an exact "effective amount." However, an appropriate effective amount can be determined by one of ordinary skill in the art using only routine experimentation.

Various delivery systems are known and can be used to administer the pharmaceutical composition of the invention, e.g., encapsulation in liposomes, microparticles, microcapsules, recombinant vectors capable of expressing the betanodavirus B2 protein. Methods of introduction include, but are not limited to, intratumoural, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

In some embodiments, the method for treating lung cancer includes administering the pharmaceutical composition to the subject via intratumoural injection.

Betanodavirus are the causative agents of viral nervous necrosis (VNN) in fish. In RNA replication, the betanodavirus synthesizes a sub-genomic RNA3 from the 3' terminus of RNA1 that encodes two proteins, B1 and B2. Hereinafter in the present application, the betanodavirus B2 protein may be abbreviated as "B2 protein" or "B2."

In some embodiments, the betanodavirus B2 protein has the amino acid sequence of SEQ ID NO: 3 or a substantially similar sequence thereof. In some embodiments, when introducing the betanodavirus B2 protein into the lung cancer cells, the betanodavirus B2 protein targets the mitochondria in both $P53^{+/+}$ and $P53^{-/-}$ lung cancer cells. However, when introducing the betanodavirus B2 protein without the amino acid sequence of "RTFVISAHAA" (SEQ ID NO: 1) into the lung cancer cells, the mutated betanodavirus B2 protein fails to target the mitochondria in both $P53^{+/+}$ and $P53^{-/-}$ lung cancer cells. While not willing to be bound by any theory, it is believed that the betanodavirus B2 protein targets the mitochondria in both $P53^{+/+}$ and $P53^{-/-}$ lung cancer cells with the fragment having the amino acid sequence of "RTFVISAHAA" (SEQ ID NO: 1). While not willing to be bound by any theory, it is believed that the betanodavirus B2 protein induces apoptosis in $P53^{+/+}$ lung cancer cells, and induces necroptosis in $P53^{-/-}$ lung cancer cells. In some embodiments, when introducing the betanodavirus B2 protein into an animal suffers from the lung tumor, the cancer cells within the solid tumor are killed and mitosis thereof is reduced. The tumor size in the treatment group is reduced for about 60% compared with normal control (100%). Furthermore, metastasis is also reduced in the treatment group.

In some embodiments, the betanodavirus B2 protein is a fusion protein. The betanodavirus B2 protein can be fused to any protein, domain or peptide to form a fusion protein to enhance its function or delivery for lung cancer treatment. For example, the B2 protein may be fused with a delivery protein, such as a protein transduction domain or a cell-penetrating peptide, to facilitate cellular intake of the B2 protein.

In some embodiments, the fragment of the betanodavirus B2 protein has the amino acid sequence of "RTFVISAHAA" (SEQ ID NO: 1) or a substantially similar sequence thereof. In some embodiments, the amino acid sequence of SEQ ID NO: 1 is the 41-50 amino acids of the amino acid sequence of SEQ ID NO: 3. While not willing to be bound by any theory, it is believed that the betanodavirus B2 protein targets mitochondria of lung cancer cells with the fragment, thus inducing cell death. Hereinafter in the present application, the amino acid sequence of SEQ ID NO: 1, or the fragment has the amino acid sequence of SEQ ID NO: 1 may also called "targeting sequence" or "signal region."

As applied to polypeptides, the term "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443-1445, herein incorporated by reference. A "moderately conservative" replacement is any change having a nonnegative value in the PAM250 log-likelihood matrix.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as Gap and Bestfit which can be used with default parameters to determine sequence homology or sequence identity between closely related polypeptides, such as homologous polypeptides from different species of organisms or between a wild type protein and a mutant thereof. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215:403-410 and Altschul et al. (1997) Nucleic Acids Res. 25:3389-402, each herein incorporated by reference.

As can be readily appreciated by persons ordinarily skilled in the art, the B2 protein or the fragment thereof can be encoded by various different nucleic acid molecules. Preferably, the nucleic acid molecule encoding the betanodavirus B2 protein or the fragment may have a nucleic acid sequence which can be transcribed and/or translated in cells of the subject in need of such treatment, especially in lung cancer cell of the subject in need of such treatment. In some embodiments, the nucleic acid molecule has the sequence of SEQ ID NO:2 or a substantially identical sequence thereof.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 95%, and more preferably at least about 96%, 97%, 98% or 99% of the nucleotide bases, as measured by any well-known algorithm of sequence identity, such as FASTA, BLAST or Gap, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

In some embodiments, the nucleic acid molecule is operably linked to a vector, preferably an expression vector.

The term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, replication defective retroviruses, adenoviruses, replication defective adenoviruses, and adeno-associated viruses). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operably-linked. Such vectors are referred to herein as "expression vectors." Common expression vectors of utility in recombinant DNA techniques are often in the form of plasmids.

As used herein, "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell).

It will be appreciated by those skilled in the art that the design of the expression vector can depend on such factors as the choice of the host cell to be transformed, the level of expression desired, etc. A vector can be introduced into host cells to thereby produce transcripts, proteins, or peptides, including fusion proteins or peptides, encoded by the nucleic acid molecule as described herein (e.g., proteins, enzymes, mutant forms thereof, fusion proteins thereof, etc.).

In some embodiments, the nucleic acid molecule is transfected into lung cancer cells in the subject in need of such treatment.

The term "transfect" or "transfection" as used herein, in general, means delivery, or, more specifically, the transfer of the nucleic acid molecule from directly outside a cell membrane to within the cell membrane. If the nucleic acid molecule is a primary RNA transcript that is processed into messenger RNA, a ribosome translates the messenger RNA to produce a protein within the cytoplasm. If the nucleic acid molecule is a DNA, it enters the nucleus where it is transcribed into a messenger RNA that is transported into the cytoplasm where it is translated into protein. The nucleic acid molecule contains sequences that are required for its transcription and translation. These include promoter and enhancer sequences that are required for initiation. DNA and thus the corresponding messenger RNA (transcribed from the DNA) contain introns that must be spliced, poly A addition sequences, and sequences required for the initiation and termination of its translation into protein. Therefore if a nucleic acid molecule expresses its cognate protein, then it must have entered a cell.

Transfection may be accomplished by a variety of mechanical, chemical and electrical means. Mechanical means of transfection include direct microinjection, particle bombardment with DNA-gold microparticles and pressured infusion. Electrical techniques for transfection are dominated by electroporation, which involves application of a high electric field to the cells, which causes disruption of the phospholipid bilayer of the plasma membrane resulting in the formation of pores in the membrane through which extracellular materials can pass. Since the electric potential across cell membrane rises about 0.5 to 1.0 volt concurrently with the formation of pores, charged molecules such as DNA are driven through the pores in a manner similar to electrophoresis. On removal of the electric field the membrane quickly reseals leaving the cells intact. Chemical transfection involves the use of agents capable of disrupting the plasma membrane sufficiently to permit exogenous materials such as therapeutic agents to cross.

In some embodiments, accordingly, the pharmaceutical composition further includes a transfection agent which facilitates transfection of the nucleic acid molecule into lung cancer cells in the subject in need of such treatment.

The term "transfection agent" refers to agents which are designated to transfect other molecules into cells, like for example DNA, RNA. For example, the transfection reagent may include DEAE dextran, calcium phosphate, polyethylenimine (PEI) and lipids. Preferably, the transfection reagent is PEI.

The following examples are given for the purpose of illustration only and are not intended to limit the scope of the present invention

Example I: B2 Protein Targets Lung Cancer Cell Mitochondria

Cell Culture

Two human non-small cell lung cancer cell lines were used for experiments: the epithelial cell line A549 (ATCC, CCL-185™; with wild type P53 expression [P53$^{+/+}$]) and line NCI-H1299 (ATCC, CRL-5803™; without P53 expression [P53$^{-/-}$]). Cells were cultured in DMEM medium supplemented with 10% fetal bovine serum, 100 units/mL penicillin, and 100 µg/mL streptomycin (Invitrogen) at 37° C. in an atmosphere of 5% $CO_2$ in 10 $cm^2$ Petri dishes or 6 well culture plates.

Plasmid Construction

The nucleic acid molecule encoding the full-length B2 protein (B2), and a comparative nucleic acid molecule encoding the B2 protein but without the fragment having the amino acid sequence of SEQ ID NO: 1 (ΔB2), were separately cloned into the pcDNA3.1 vector (Clontech Laboratories, Palo Alto, Calif.), the p3XFLAG-myc-CMV-26 vector (Sigma), and the pEYFP-C1 vector (Clontech), with the enhanced yellow fluorescent protein (EYFP).

Cell Transfection

Polyethylenimine (PEI; Sigma Aldrich, 408727) was used as the transfection agent. For cell transfection, 4×10$^5$ cells were seeded in 6-well culture plates. On the following day, 3.2 µg of recombinant plasmid was mixed with 3.2 µg of PEI, and the transfection procedure was carried out according to the manufacturer's instructions.

Preparation of Mitochondria from B2-Transfected Cells

A549 and H1299 cells were seeded in 60-mm diameter culture dishes with 4 mL of medium (105 cells/mL) for 24 h. These cells were then transfected with EYFP or EYFP-B2 for 48 h. At each change of the culture medium, 1 mL of medium was removed. Mitochondria were isolated by the following process. Briefly, cells (2×10$^6$) were washed with PBS and homogenized in 0.3 mL of mitochondria isolation buffer (0.35 M mannitol, 10 mM HEPES, pH 7.2, 0.1% bovine serum albumin) using a glass homogenizer. Unbroken cells and nuclei were pelleted by centrifugation (600 g for 5 min at 4° C.). Then, the mitochondrial pellet was isolated by centrifugation (10,000 g for 10 min at 4° C.) and the supernatant was collected and mixed with 25 µL of 10×SDS sample buffer. Samples (50 µL) were boiled and subjected to western blot analysis.

Mitochondrial Staining Assay

To track changes in mitochondrial morphology, cells were transfected as described above. After culture for 48 h, cells were stained with MitoTracker Red CM-H2XRos (Invitrogen) in accordance with the manufacturer's instructions. Then, cells were analyzed by fluorescence microscopy, with excitation at 488 nm green fluorescence measured with a 515-nm long-pass filter, and with 510 nm excitation and red fluorescence measured with a 590-nm long-pass filter.

Protein Extraction and Western Blot Analysis

After various times of incubation, cells were rinsed with 1×PBS, 3% BSA, and 0.1% Tween-20, then lysed with 0.05% SDS, boiled for 2 min, and centrifuged (10,000 g at 48° C. for 10 min). The supernatant was diluted with 6×Laemmli loading buffer and boiled for 2 min prior to loading. Proteins were resolved by 10% sodium dodecyl sulfate—polyacrylamide gel electrophoresis, and electroblotted onto nitrocellulose membranes. The membranes were incubated in a blocking solution (3% BSA, 0.1% Tween-20, 1×TBS) for at least 1 h at room temperature (RT). Immunoblotting was performed with the following antibodies overnight at 4° C.: anti-FLAG primary monoclonal antibodies (Sigma), Bax, Bcl2, Bid, Bak, LC3, P53, P53 ser15, P53 ser392, P53 ser46, RIP3, beclin-1, and caspase-3 (Cell Signaling Technology). Then, membranes were washed with TBS and 0.1% Tween-20, and incubated for 1 h at RT with the secondary antibody (horse radish peroxidase, DakoCytomation) at a dilution of 1:2000. After washing, the membranes were developed using the enhanced chemiluminiscence system (ECL, Amersham Life Sciences). The signals were quantified using ImageJ software and ß-actin was used as a loading control.

3D-Structure Prediction

SWISS-MODEL Repository (SMR) and Phyre2 web portal are a database of annotated 3D protein structure models generated by the automated SWISS-MODEL homology modeling pipeline (Bienert S et al. Nucleic Acid Res. 2017; 45:D313-D319; and Biasini M et al. Nucleic Acid Res. 2014; 42:W252-W258) and Phyre2 web portal system (Kelley L A et al. Nat Protoc. 2015; 10:845-858.). In the 3D-structure prediction, the full length B2 protein (1-75 aa) and B2 mitochondrial targeting domain (36-61 aa) alone sequence for comparing from either SWISS-MODEL Repository system or Phyre2 web portal system. Two systems we have found that received very similar results. Then further confirmed the 3D-structure of protein B2 to published alpha-nodavirus protein B2 in dimer form structure (Chao J A et al. Nat Str Mol Bio. 2005; 12:952-957.) that still received the consistent result, have shown the alpha helix structure.

Statistical Analysis

All western blot images are representative of at least three independent experiments. The level of ROS production (H2DCFDA assay) and percentage of Annexin-V and PI-fluorescein-positive cells was determined by counting 200 cells per sample. Each result is expressed as the mean±SEM. Data were analyzed using the paired or unpaired Student's t-test, as appropriate. For comparison of group means, a P value less than 0.05 was considered statistically significant.

Results

In these experiments, EYFP-B2 and EYFP-ΔB2 are used to determine whether the B2 protein can target the mitochondria of human lung cancer cell lines A549 (P53$^{+/+}$) and H1299 (P53$^{-/-}$).

The localization of EYFP, EYFP-B2 and EYFP-ΔB2 are measured with green fluorescence using MitoTracker. The results show green fluorescence in the mitochondria of cells transfected with the full-length EYFP-B2 (FIGS. 1A and 1Ag-1Ai: A549 cells; p-r: H1299 cells). In contrast, cells of the EYFP group (FIG. 1A and FIG. 1Aa-1Ac: A549 cells; d-f: H1299 cells) and the EYFP-ΔB2 group (FIG. 1A and FIG. 1Aj-1Al: A549 cells; m-o: H1299 cells) have green fluorescence almost entirely in the cytoplasm. The B2 protein construct used for mitochondrial targeting is shown in FIG. 1B.

The predicted 3D-structure of full length (1-75 aa) B2 protein and the B2 mitochondria targeting domain (36 aa, as a major alpha helix confirmation) are shown in FIG. 1C. The mitochondrial localization of B2 is further examined by performing western blotting analysis at 48 h post-transfection (FIG. 1D).

These results confirm that B2 targets the mitochondria in A549 and H1299 cells with the fragment thereof (e.g., the fragment having the amino acid sequence of SEQ ID NO: 1).

Example 2: B2 Protein Induces Apoptosis in A549 ($P53^{+/+}$) Cells and Necroptosis in H1299 ($P53^{-/-}$) Cells Assays for Apoptosis and Necrosis The Annexin V-FITC/Propidium iodide (PI) flow cytometric assay was used to measure early and late apoptosis, according to the manufacturer's instructions (Annexin V-FITC/PI, Rocha). Briefly, A549 and H1299 cells were transfected with FLAG or FLAG-B2 plasmids for 48 h at 37° C., then washed twice with cold PBS, and centrifuged at 1000 rpm for 5 min. The harvested cells were resuspended in 200 μL binding buffer that contained 10 μL Annexin V-FITC. After 15 min, the cells were washed twice and resuspended in 300 μL binding buffer, and 10 μL of PI was added. Then, the cells were immediately analyzed by flow cytometry using a FACS Vantage cell sorter (Becton-Dickinson, San Jose, Calif., USA). PI red fluorescence was measured using a 650-nm long-pass filter. Apoptotic and necroptotic cells have higher PI fluorescence ($PI^+$) than intact cells ($PI^-$). Each analysis examined at least 10,000 cells in the gated region, based on light scattering properties. Fluorescence data are displayed on one or two major scales.

Results

Figure 2:
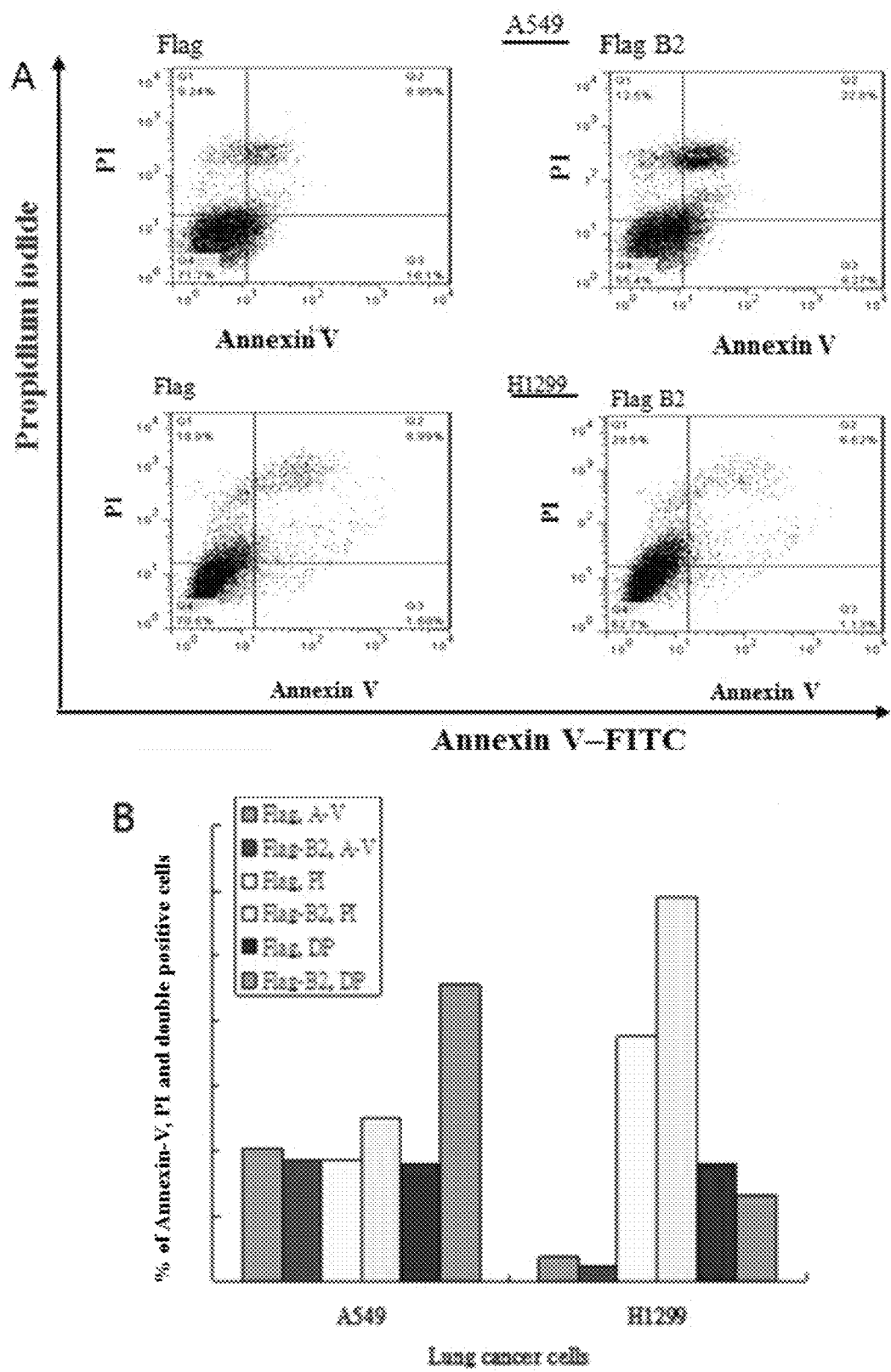
FIG. 2: B2 protein induces apoptosis in A549 cells, but induces necroptosis in H1299 cells. (A) Representative flow cytometry results at 48 h post-transfection. Fluorescence of Annexin-V and PI were measured in 10,000 cells. Annexin-V-FITC$^+$ cells indicate early apoptosis and PI$^+$ cells indicate late apoptotic/secondary necrosis. (B) Quantitation of the percentage of viable cells (Annexin-V-FITC$^+$ and PI$^+$) from flow cytometry experiments.

The mechanism(s) by which the B2 protein induces cell death in both lines of lung cancer cells were determined by use of flow cytometric analysis with Annexin-V-FITV and PI staining (FIG. 2). The results show that B2 protein induces apoptosis in 13% of A549 cells (FIGS. 2A and 2B), but induces necroptosis in 10% of H1299 cells (FIGS. 2A and 2B). Hence, the method of the invention can be used for treatment of both $P53^{+/+}$ and $P53^{-/-}$ lung cancers.

Example 3: B2 Protein Kills Lung Cancer Cells and Reduces Tumor Size

Tumor Induction

Respectively, A549 tumor cell lines ($1\times10^6$/mouse in 100 μL 0.9% saline) were injected into the flank of male NOD SCID mice by subcutaneous injection.

B2 Gene Treatment

B2 gene and control drug (5-FU) were administrated via intratumoural injection (thrice per week; 12 times injection). After 4 weeks treatment, all mice (n=4-6/group) were sacrificed. Then tumor tissues were collected for H&E staining.

Figure 3:
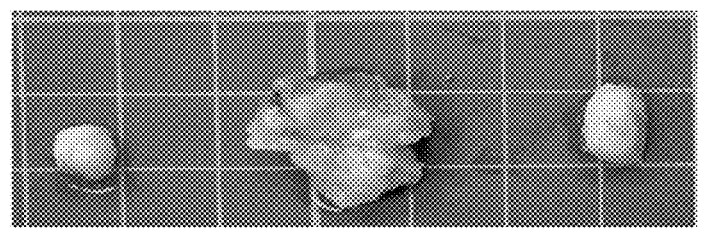
FIG. 3: The B2 expression effectively kills the A549 cell within solid tumor.
Figure 4:
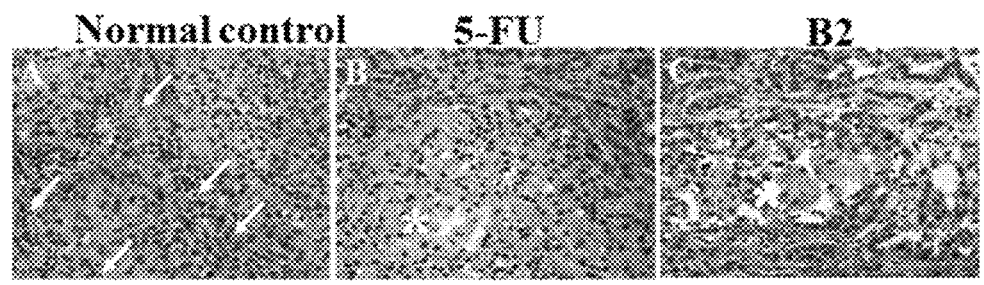
FIG. 4: The B2 expression effectively reduces mitosis.

The B2 expression can effectively kill the A549 cell within solid tumor (FIG. 3) and reduces mitosis (FIG. 4; indicated by arrowheads in FIG. 4A). The tumor size in the B2 treatment group is reduced for about 60% compared with normal control (100%). Besides, metastasis is also reduced in the B2 treatment group.

Figure 5:
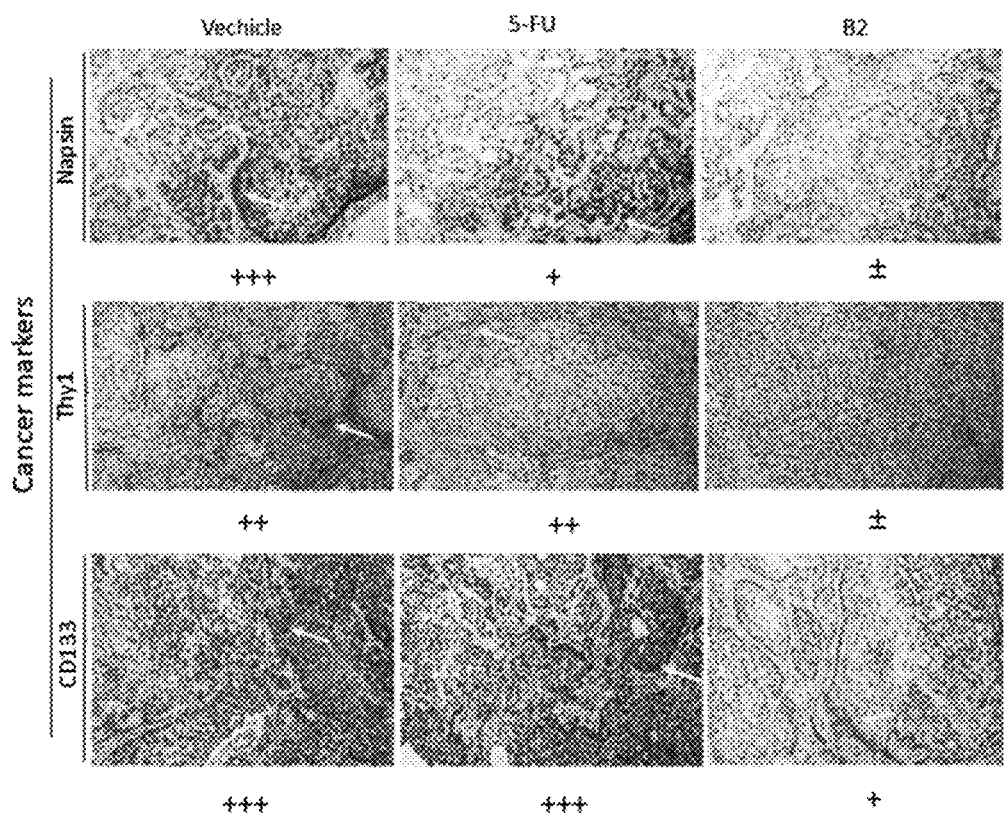
FIG. 5: Immunostaining result of cancer markers for cell migration and invasion in lung cancer cells treated with B2 gene.

B2 gene can express a B2 protein in lung cancer cells (in A549 cell line) that triggers cell death and reduces cell migration and invasion. The cancer markers for cell migration and invasion such as Napsin, Thy1 and CD133 were identified by immunostaining with specific monoclonal antibodies in solid tumors (FIG. 5).

These results show that the pharmaceutical composition of the present invention can be used for lung cancer treatment. The pharmaceutical composition may reduce the tumor size and metastasis.

While the present disclosure has been described and illustrated with reference to specific embodiments thereof, these descriptions and illustrations are not limiting. It should be understood by those skilled in the art that various changes may be made and equivalents may be substituted without departing from the true spirit and scope of the present disclosure as defined by the appended claims. The illustrations may not be necessarily drawn to scale. There may be distinctions between the artistic renditions in the present disclosure and the actual apparatus due to manufacturing processes and tolerances. There may be other embodiments of the present disclosure which are not specifically illustrated. The specification and drawings are to be regarded as illustrative rather than restrictive. Modifications may be made to adapt a particular situation, material, composition of matter, method, or process to the objective, spirit and scope of the present disclosure. All such modifications are intended to be within the scope of the claims appended hereto. While the methods disclosed herein have been described with reference to particular operations performed in a particular order, it will be understood that these operations may be combined, sub-divided, or re-ordered to form an equivalent method without departing from the teachings of the present disclosure. Accordingly, unless specifically indicated herein, the order and grouping of the operations are not limitations of the present disclosure.

What is claimed is:

1. A method for treating lung cancer in a subject in need of such treatment, comprising:

administering to the subject a pharmaceutical composition comprising an effective amount of a betanodavirus B2 protein or a nucleic acid molecule encoding the betanodavirus B2 protein, and optionally a pharmaceutically acceptable carrier or excipient, wherein the betanodavirus B2 protein has the amino acid sequence of SEQ ID NO: 3 or a substantially similar sequence thereof, and the nucleic acid molecule has the sequence of SEQ ID NO: 2 or a substantially identical sequence thereof.

2. The method of claim 1, wherein the lung cancer is non-small cell lung cancer.

3. The method of claim 1, which comprising administering to the subject via intratumoural injection.

4. The method of claim 1, wherein the nucleic acid molecule is operably linked to a vector.

5. The method of claim 4, which comprises transfecting the nucleic acid molecule into lung cancer cells in the subject in need of such treatment.

6. The method of claim 5, wherein the pharmaceutical composition further comprises a transfection agent.

7. The method of claim 1, wherein the betanodavirus B2 protein is a fusion protein.

* * * * *